United States Patent [19]

Krauter

[11] Patent Number: 5,031,510
[45] Date of Patent: Jul. 16, 1991

[54] EVACUATION SPRING FOR HYDRAULIC/PNEUMATIC MUSCLE

[75] Inventor: Allan I. Krauter, Syracuse, N.Y.

[73] Assignee: Welch Allyn, Inc., Skaneateles Falls, N.Y.

[21] Appl. No.: 497,602

[22] Filed: Mar. 22, 1990

[51] Int. Cl.$^5$ ............................................. F01B 19/04
[52] U.S. Cl. ................................................ 92/92; 92/94; 92/132; 92/130 A; 128/4; 403/316; 403/341
[58] Field of Search ................ 92/90, 91, 92, 94, 247, 92/130 R, 130 C, 132, 130 A, 40; 403/316, 317, 341, 353; 128/4

[56] References Cited

U.S. PATENT DOCUMENTS

| | | | |
|---|---|---|---|
| 1,107,889 | 8/1914 | Burns | 403/353 |
| 2,399,133 | 4/1946 | Midling | 403/316 |
| 2,483,088 | 9/1946 | DeHaven | 92/90 |
| 3,861,814 | 1/1975 | Fisher | 403/316 X |
| 4,571,788 | 2/1986 | Bruengger | 403/316 X |
| 4,645,373 | 2/1987 | Purdy | 403/341 |
| 4,664,232 | 5/1987 | Takagi et al. | 92/90 X |
| 4,678,360 | 7/1987 | Miller | 403/353 |
| 4,762,118 | 8/1988 | Lia et al. | 128/4 |
| 4,793,726 | 12/1988 | Sword | 403/353 X |
| 4,794,912 | 1/1989 | Lia | 92/92 X |
| 4,841,845 | 6/1989 | Beullens | 92/90 X |
| 4,865,017 | 9/1989 | Shinozuka | 128/4 |
| 4,962,751 | 10/1990 | Krauter | 128/4 |

FOREIGN PATENT DOCUMENTS 58-81205  5/1983  Japan ..................................... 92/90

Primary Examiner—John T. Kwon
Assistant Examiner—John Ryznic
Attorney, Agent, or Firm—Wall and Roehrig

[57] ABSTRACT

A hydraulically or pneumatically actuated muscle has an elongated elastomeric bladder that is covered by a tubular sheath. A fluid conduit is coupled to the bladder to supply hydraulic or pneumatic pressure. A coil tension spring is attached to a distal terminator of the muscle and extends to the distal end of a compression tube covering the bladder and braid. The evacuation spring draws the braid and bladder towards their fully extended state when fluid pressure is relieved and ell-shaped retaining pin in the muscle terminator has one end that extends radially outward to lodge between turns of the evacuation spring. Split shoulder washers secure the proximal and distal ends of the compression tube.

12 Claims, 2 Drawing Sheets

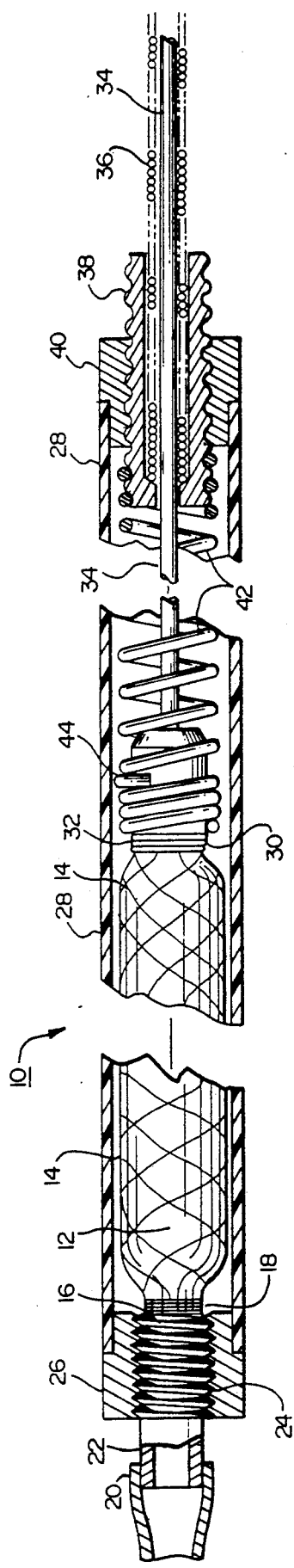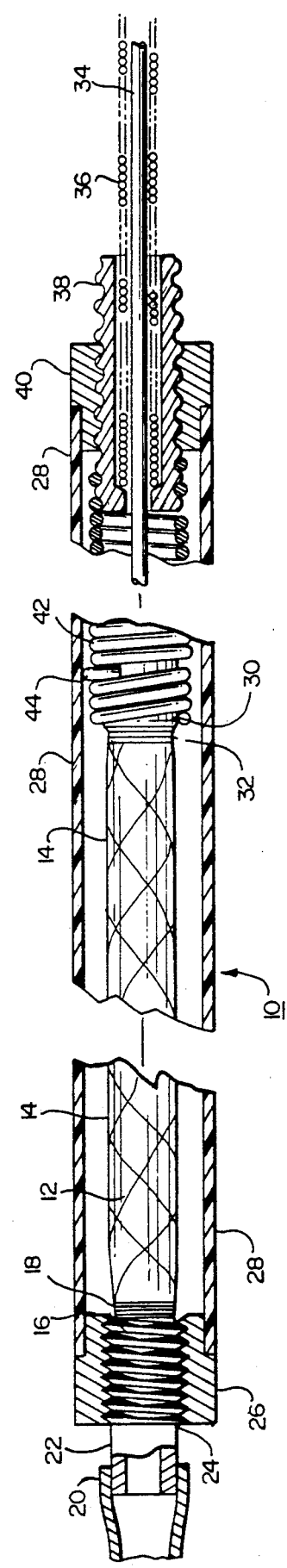

EVACUATION SPRING FOR HYDRAULIC/PNEUMATIC MUSCLE

BACKGROUND OF THE INVENTION

This invention relates to hydraulically or pneumatically actuated muscles, that is, devices which convert a fluid pressure into a tensive force. The invention is more specifically directed to structure for biasing the muscle to its elongated or extended state. The invention is also directed to the serviceable attachment of the distal muscle terminator to its associated control cable.

Hydraulic muscles can be favorably employed in an elongated flexible probe such as a borescope or endoscope for actuating its articulation or steering section. With the use of hydraulic muscles, the conventional long steering cables can be eliminated. This use of a hydraulic muscle in a borescope or endoscope is described in U.S. patent application Ser. No. 357,806, now U.S. Pat. No. 4,962,751 filed May 30, 1989, and having a common assigned herewith. Another fluid dynamic muscle in a borescope or endoscope is described in U.S. Pat. No. 4,794,912, granted Jan. 3, 1989. Fluid dynamic articulation and steering for a borescope or endoscope offers a distinct improvement over the conventional system of steering cables, permitting much more accurate and precise positioning of the viewing end of the instrument within the cavity to be inspected.

The hydraulic or fluid dynamic muscle is made of an elongated tubular bladder which is encased in an elongated tubular braid member disposed over it. Terminators are provided at the proximal and distal ends of the muscle to seal the ends of the bladder and to provide a place for mechanical attachment between the ends of the braid member and the mechanical members to which they are to transfer force, e.g., a cable or a muscle sheath. The braid permits the bladder within the muscle to expand laterally when hydraulic pressure is applied to it. However, as the braid and bladder expand radially, the braid contracts axially and generates an axial tensive force.

The fluid dynamic muscles are used in pairs, with one of the muscles being actuated to deflect the borescope steering section in one direction (i.e. to the left) and the other muscle being actuated to deflect the steering section in the other direction (i.e. to the right). With this arrangement the tension from the muscle that is actuated extends the muscle that is not being actuated and expels the fluid from it. The bladder and braid alone typically are not effective to stretch the muscle back to an elongated state when the hydraulic or pneumatic pressure is relieved. Therefore, there is a constant tension on both steering cables of each pair of cables. This can make steering somewhat difficult, can reduce the amount of articulation of the steering section, and can require higher pressures to be employed than is desirable in view of the need to avoid leakage of hydraulic fluid from the muscles.

Also, under current techniques, access to the muscle terminator that connects to the cable terminator is difficult, once the muscle is installed. Further, it is difficult to detach and reattach the cables to the muscle terminators, and special tools may be required to do so.

OBJECTS AND SUMMARY OF THE INVENTION

It is an object of this invention to provide an improved hydraulic or pneumatic muscle having an internal bladder, an external braid, and a terminator disposed at the distal end to connect with a control cable, and which avoids the drawbacks of the prior art.

It is another object of this invention to provide a hydraulic muscle with a stretching force to bias the same towards its elongated or extended condition.

It is still another object of this invention to provide a retainer mechanism to facilitate assembly and disassembly of the muscle and associated control cable.

According to one aspect of this invention, the fluid dynamic muscle is provided with a coil tension spring for drawing the braid and bladder toward their fully-extended state when fluid pressure is relieved from the bladder. The muscle itself comprises an elongated elastomeric bladder, a fluid conduit coupled to the proximal end of the bladder to supply hydraulic or pneumatic pressure to the interior of the bladder, and a tubular braid disposed over the bladder. The braid is made up of substantially inextensible filaments that cover the bladder. The braid increases in diameter when fluid pressure is applied to the bladder within it, but is self-restrained to contract axially and creates a tensile force that is transmitted to an associated control cable.

A muscle terminator is fitted into the distal ends of the bladder and braid, to seal the distal ends of the bladder and to transmit tensile force between the braid and the proximal end of the control cable, which has a cable sheath disposed over it.

To support the cable sheath, a compression tube is disposed radially outside the braid and extends from the proximal end of the braid, where it is attached to the braid, to a point beyond the distal end of the braid as considered when the braid and bladder are in their fully extended state. At the distal end of the compression tube is supported a cap, in the form of, e.g. a shoulder washer with internal threads, and a threaded nipple supported therein. The control cable passes through this nipple and the proximal end of the cable sheath is held against it.

A coil spring is attached to the distal end of the compression tube, e.g., by screwing one end of it onto the threaded nipple, and is also attached at its other end onto the muscle distal terminator. The evacuation spring is favorably attached to the terminator by means of an ell-shaped retainer pin that also retains the cable terminator within an axial bore of the muscle terminator.

The evacuation spring serves to elongate the muscle and to evacuate any remaining air or hydraulic fluid when the fluid pressure is relieved. This hastens the return of the muscle to its elongated condition and reduces frictional forces in the slack cable, e.g. between the cable and sheath and also within the associated steering section.

This means that frictional buildup of the relaxed muscle and cable does not occur in the cable sheaths or in the bending or steering section. The opposed or active muscle does not have to overcome that frictional force, but only needs to meet the additional force of its own evacuation spring, which is typically about ten percent of the muscle force.

Borescopes which employ a hydraulic muscle with evacuation spring have exhibited an increase of at least 20 degrees in the range of steering deflection obtainable without any increase in hydraulic capacity or pressure.

The use of the evacuation spring in combination with a cable retention pin permits easy serviceability of the connection of the cable and muscle terminator, and also facilitates connection of the evacuation spring to the muscle terminator.

The above and many other objects, features, and advantages of this invention will become more apparent from the ensuing description of a preferred embodiment which should be read in connection with the accompanying Drawing.

BRIEF DESCRIPTION OF THE DRAWING

FIG. 1 is a longitudinal sectional in view of a hydraulic muscle according to one embodiment of this invention, the muscle being shown in its inflated, contracted state.

FIG. 2 is a longitudinal sectional view of the hydraulic muscle in its evacuated, elongated state.

DETAILED DESCRIPTION OF THE PREFERRED EMBODIMENT

Figure 7:
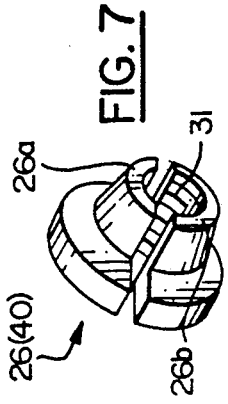
FIG. 7 is a perspective view of the shoulder washer employed at the proximal and distal ends of the compression tube.

With reference to the Drawing, and initially to FIGS. 1 and 2, a hydraulic muscle 10 has an elongated elastomeric bladder 12 and a tubular braid 14 that is disposed over the bladder 12. The braid for the hydraulic muscle is formed of interwoven substantially inextensible filaments, such that when the bladder 12 is inflated by having hydraulic fluid applied to it under pressure, the bladder 12 and braid 14 will expand in diameter, but shorten axially, to generate a tensive force. The bladder and braid 12, 14 are secured at their proximal ends to a proximal terminator 16, which can be of the type generally described in copending U.S. patent application No. 475,822 having a common assignee. The proximal ends of the braid and bladder are secured with a coil of fishline 18 or equivalent cord. The fishline provides a radially inward force to hold the bladder in sealing engagement against the terminator 16 and mechanically binds the braid 14 to the terminator 16. Standard fishline wraps and an appropriate adhesive can be employed. A hydraulic line 20 fits onto a hydraulic nipple 22 of the terminator 16, and communicates fluid pressure to the interior of the bladder 12. The terminator 16 also has a threaded anchor portion 24 between the fishline wrap 18 and the nipple 22. A shoulder washer 26 that has an internal thread engages the anchor portion 24 and supports the proximal end of a compression tube 28 that extends over the length of the braid and bladder 14, 12. The shoulder washer 26 is slit axially as is shown in FIG. 7, with two semiannular halves 26a and 26b. Polytetrafluoroethylene (PTFE) is a suitable material for the compression tube 28. A distal terminator 30 is attached to the distal ends of the bladder 12 and braid 14, favorably employing a wrap 32 of fishline or equivalent cord. A structure of the distal end terminator 30 will be described in greater detail with reference to FIGS. 3, 4 and 5.

Figure 3:
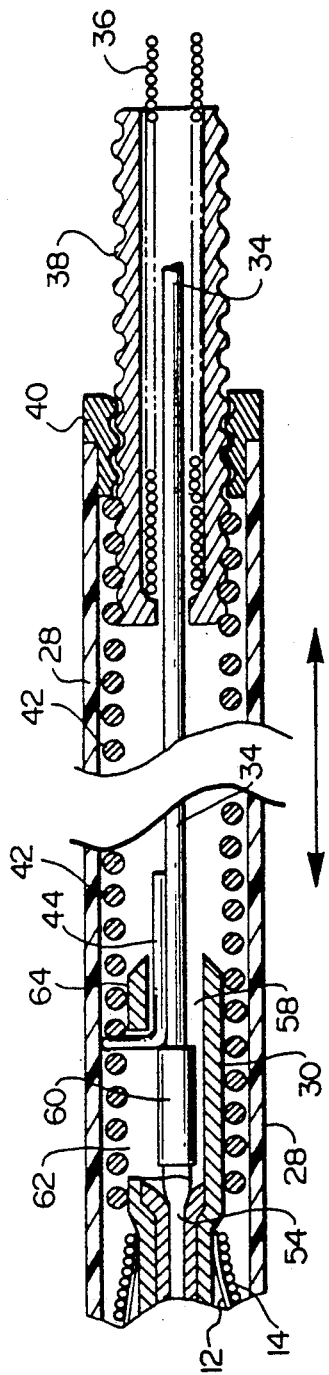
FIG. 3 is a detailed sectional view of a distal end of the hydraulic muscle of this embodiment.
Figure 5:
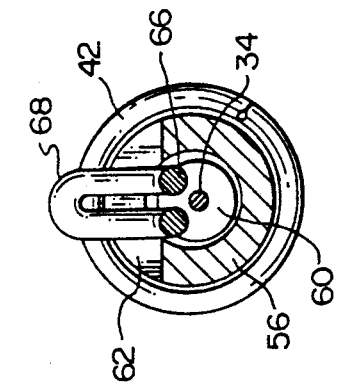
FIG. 5 is a cross section taken at 5—5 of FIG. 4.
Figure 4:
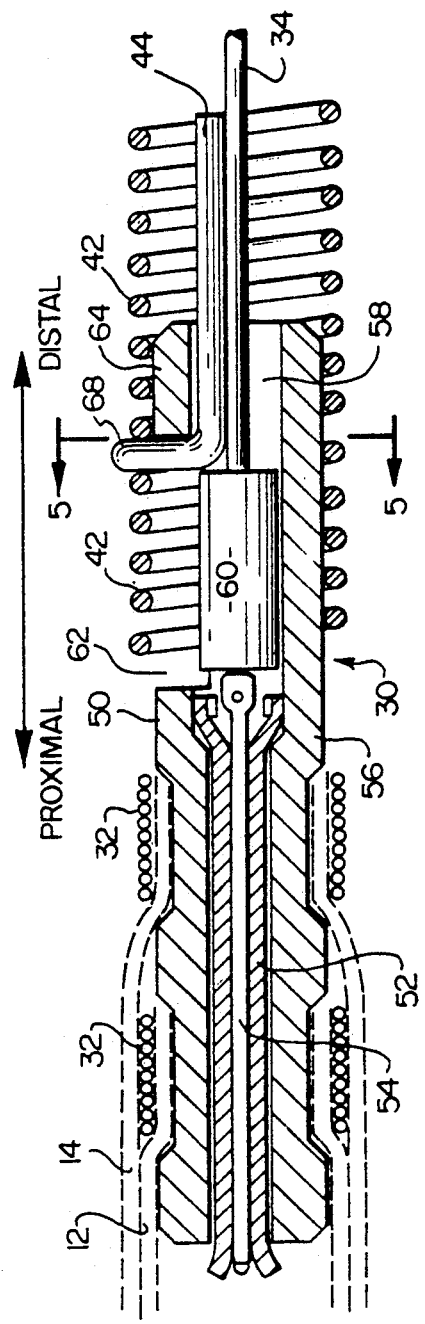
FIG. 4 is a detailed sectional view of the distal end terminator of the hydraulic muscle, showing the evacuation spring and retainer assembly.

A control cable 34 has its proximal end attached to the distal terminator 30, and extends out through the distal end of the muscle assembly, where it passes through a flexible tubular cable sheath 36. The cable 34 passes through an externally threaded nipple 38 that compressively supports the proximal end of the sheath 36. A distal split shoulder washer 40 has an internal thread 31 that engages the thread of the nipple 38, and also fits into the distal end of the compression tube 28. This split shoulder washer 40 has the same design as the split shoulder washer 26 in FIG. 7. A coil evacuation spring 42 is threaded onto the proximal end of the nipple 38 and also engages a retainer pin 44 on the distal terminator 30. This spring 42 applies a tension onto the bladder 12 and braid 14 of the muscle. As shown in FIG. 1, when hydraulic pressure is applied through the line 20 the bladder 12 and braid 14 shorten axially, drawing in the cable 34, and stretching the spring 42. Then, as shown in FIG. 2, when the pressure is relieved to the line 20, the evacuation spring 42 pulls the braid 14 and bladder 12 back to an elongated state. This assists in the evacuation of fluid from within the bladder 12, and also relieves some of the force on the slackened control cable 34. As shown in FIGS. 3-5, the distal end terminator 30 has a sealing body 50 containing an axial bleed seal 52 that communicates with the interior of the bladder 12, and a seal pin 54 that is contained therewithin. The bleed seal 52 and pin 54 are the subject of copending U.S. patent application No. 476,945, which has a common assignee herewith, now U.S. Pat. No. 4,974,497 granted Dec. 4, 1990. The terminator 30 also has an anchor portion that is distal of the wraps 32. This anchor portion 56 has an axial bore 58 into which is fitted a generally cylindrical cable terminator 60 that is soldered onto the proximal end of the cable 34. Access to the bore 58 is achieved through a cutout 62 on one side of the anchor portion 56, the cutout 62 being spaced somewhat proximally from the distal end to form a retaining bar 64 at the distal end. Here the retainer 44 which is in the form of a generally L-shaped pin is inserted to lodge against the retaining bar 64 and also against the cable terminator 60 to prevent it from being pulled out through the bore 58.

Figure 6:
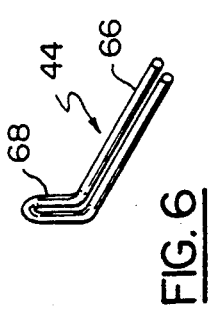
FIG. 6 is a perspective view of the retainer pin employed with the hydraulic muscle of this embodiment.

The retaining pin 44 can favorably have the form as shown in FIG. 6. The retainer 44 can be formed of a length of wire bent into a U-shaped member, and then bent again into the form of a ell. The pin has a longer portion 66 formed by the parallel free ends, and a shorter portion 68 formed by the bend or bight. Here, the bight 68 is perpendicular to the plane of the two free ends. The bight protrudes radially out the cutout 62 a distance sufficient that it can engage securely between turns of the spring 42.

Assembly of the hydraulic muscle is relatively straightforward, and does not require any special tools. The cable terminator 60 is inserted through the bore 58 and then out through the side cutout 62, after which the retainer pin 44 can be inserted. Then the cable terminator 60 is pushed back into cutout 62 and is held in place by the pin 44. When in position, the cable terminator 60 holds the seal pin 54 in place, preventing it from moving appreciably in the distal direction. The evacuation spring is attached to the muscle terminator 50 by screwing the spring over the terminator and engaging the bight end 68 of the pin 44. Then, the nipple 38 is screwed into the distal end of the spring 42.

Completion of the muscle assembly is as follows. The compression tube 28, which prior to starting the assembly, had been placed on the tube 20 proximally of the anchor portion 24, is slid distally over the muscle. The nipple 38 is pulled distally, after which the split shoulder washers 26 and 40 are seated onto the threads of anchor portion 24 and nipple 38. The proximal end of the compression tube 28 is then slid over the split shoulder washer 26 and the split shoulder washer 40 is inserted, along with nipple 38, into the distal end of the compression tube 28.

The tension on the spring 42 holds the nipple 38 and its associated split shoulder washer 40 in engagement with the PTFE compression tube 28. The evacuation spring not only provides the benefit of evacuation of the muscle, but it also prevents the free ends 66 of the retainer pin from touching the compression tube 28. The spring 42 also maintains the cable 34 near the center of the compression tube 28, and supplies radial stabilization to the compression tube.

Disassembly of the hydraulic muscle 10 for servicing is also straightforward, and does not require special tools. Initially, the nipple 38 and split shoulder washer 40 are pulled axially away from the compression tube, so that the split shoulder washers 26 and 40 can be removed from the anchor portion 24 and nipple 38. Then the compression tube 28 is slid proximally over the anchor portion 24 and onto the tube 20. The spring 42 is unscrewed off the muscle terminator 30. At that point the retainer pin 44 is removed from the bore 58 and the cable terminator 60 can be removed from the muscle terminator by pulling the cable 34 distally. With the seal pin 54 unblocked, the seal pin 54 can be removed from the terminator for bleeding air, etc. from the bladder 12. Then the pin 54 can be reinserted, and the cable terminator 60 and pin 44 reinserted in the muscle terminator 30. After this, the spring 42 can be reattached, as described previously.

While this invention has been described in detail with reference to a preferred embodiment, it should be understood that the invention is not limited to that precise embodiment. Rather many modifications and variations will present themselves to those of skill in the art without departing from the scope and spirit of this invention, as defined in the appended claims.

What is claimed is:

1. A fluid dynamic muscle which comprises an elongated elastomeric bladder, fluid conduit means coupled to a proximal end of the bladder for communicating fluid pressure to an interior of the bladder, a tubular braid formed of a plurality of substantially inextensible filaments and covering said bladder therewithin to expand laterally when fluid pressure is applied to it, but restraining the bladder such that as the braid increases in diameter it contracts axially, a control cable, a flexible, substantially incompressible cable sheath disposed over said cable, a distal-end terminator fitting the distal ends of the bladder and braid for sealing the distal end of the bladder and providing a mechanical attachment point for said control cable for transmitting tensile force between said braid and said control cable, a compression tube over said braid and extending axially from the proximal end of said braid beyond the distal end thereof when in a fully-extended state, cable sheath support means mounted at a distal end of said compression tube and supporting a proximal end of said cable sheath, and a coil tension spring within the compression tube having one end mounted onto the distal end of the compression tube and another end mounted on said distal-end terminator for drawing said braid towards its fully extended state when the fluid pressure is relieved from said bladder.

2. The fluid dynamic muscle of claim 1 wherein said cable sheath support means includes a cap fitting the distal end of said compression tube and a threaded nipple disposed axially through said cap, the distal end of said coil spring being secured onto threads of said nipple.

3. The fluid dynamic muscle of claim 2 whereon said cap is provided with a shoulder having a diameter substantially that of the outer diameter of the compression tube and a neck having a diameter substantially that of the inner diameter of the compression tube.

4. The fluid dynamic muscle of claim 3 wherein the cap has been cut or split axially.

5. The fluid dynamic muscle of claim 1 wherein said distal end muscle terminator includes a distal anchor portion that has an axial bore to receive a substantially cylindrical cable terminator on a proximal end of said cable, and a cutout to one side of the anchor portion permitting access to said bore, the cutout being spaced axially from the distal end of the anchor portion to leave a transverse bar portion distal of said cutout.

6. The fluid dynamic muscle of claim 5 further comprising an ell-shaped retainer pin which is inserted into said cutout to lodge between the cable terminator and said bar portion, with one leg extending generally axially along said cable and another leg protruding generally radially out of said cutout.

7. The fluid dynamic muscle of claim 6 wherein said other leg protrudes between turns of said spring at its proximal end to retain the same on said muscle terminator.

8. The fluid dynamic muscle of claim 6 wherein said ell-shaped retainer pin is a bent U-member having a pair of parallel free-end members forming said one leg and a bight forming said other leg.

9. A distal-end muscle terminator and control cable retainer pin for a fluid dynamic muscle of the type in which an elongated elastomeric tubular bladder has an elongated tubular braid member disposed thereover, a fluid conduit communicates with an interior of the bladder, and a distal end of said braid member transmits tensile force to a control cable that has a generally cylindrical cable terminator at its proximal end; comprising a distal-end muscle terminator that fits into respective distal ends of the bladder and braid member for providing mechanical attachment to said cable terminator for transmitting tensile forces between the braid member and the cable, the muscle terminator including a distal anchor portion having an axial bore to receive said cable terminator and a cutout to one side of the anchor portion permitting access to said bore, the cutout being spaced axially from the distal end of the anchor portion to leave a transverse bar portion distal of said cutout; and an ell-shaped retainer pin which is inserted into said cutout to lodge between the cable terminator and said bar portion, with one leg portion extending generally axially along said cable and another leg portion extending generally radially out said cutout.

10. The muscle terminator and retainer pin of claim 9 wherein said ell-shaped retainer pin is a bent U-member having a pair of parallel free ends forming said one leg and a bight forming said other leg.

11. The muscle terminator and retainer pin of claim 10 wherein said bight is bent in the direction generally perpendicular to a plane defined by the parallel free ends.

12. The muscle terminator and retainer pin of claim 10 wherein said bight protrudes out of said cutout a sufficient distance to penetrate between turns of a coil spring disposed on a circumferential surface of said anchor portion.

* * * * *